United States Patent
Wedekamp

(10) Patent No.: US 6,313,468 B1
(45) Date of Patent: Nov. 6, 2001

(54) DEVICE FOR THE CONTINUOUS DETERMINATION OF THE UV-TRANSMISSION THROUGH FLOWING OR RUNNING MEDIA

(75) Inventor: Horst Wedekamp, Herford (DE)

(73) Assignee: Wedeco AG Water Technology, Düsseldorf (DE)

( * ) Notice: Subject to any disclaimer, the term of this patent is extended or adjusted under 35 U.S.C. 154(b) by 0 days.

(21) Appl. No.: 09/262,801

(22) Filed: Mar. 4, 1999

(30) Foreign Application Priority Data

Mar. 5, 1998 (DE) .............................................. 198 09 455

(51) Int. Cl.$^7$ ........................... G01N 21/33; G01N 21/85
(52) U.S. Cl. ........................................... 250/373; 250/372
(58) Field of Search ..................................... 250/373, 372

(56) References Cited

U.S. PATENT DOCUMENTS

| | | | |
|---|---|---|---|
| 3,566,105 | * | 2/1971 | Wiltrout ................................. 250/373 |
| 3,591,801 | * | 7/1971 | Watson ................................. 250/373 |
| 4,103,167 | * | 7/1978 | Ellner ................................. 250/432 R |
| 4,304,996 | * | 12/1981 | Blades ................................. 250/373 |
| 4,336,223 | * | 6/1982 | Hillman ................................. 422/24 |
| 4,775,794 | | 10/1988 | Behmann . |
| 5,266,280 | * | 11/1993 | Hallett ................................. 422/186.3 |

FOREIGN PATENT DOCUMENTS

| | | | |
|---|---|---|---|
| 38 36 850-A1 | * | 5/1990 | (DE) ................................. C02F/9/00 |
| 0 059 140 | | 9/1982 | (EP) . |
| 0 059 140-A1 | * | 9/1982 | (EP) ................................. G01N/21/85 |
| 2 256 043 | | 11/1992 | (GB) . |
| 2 335 033-A | * | 9/1999 | (GB) ................................. G01N/21/33 |

* cited by examiner

Primary Examiner—Constantine Hannaher
Assistant Examiner—Albert Gagliardi
(74) Attorney, Agent, or Firm—Collard & Roe, P.C.

(57) ABSTRACT

A device for determining the level of UV-transmission through a flowing media This UV-transmission is determined by measuring and evaluating the radiation intensity of a UV-radiation source radiating through a zone of the medium. The emitting surface of the UV-radiation source partly extends into the flowing medium and partly into a reference space, or borders on the medium and the space. Two UV-sensors are directed at zones of equal irradiation intensity of the radiation source emitting surface. In this case, the one UV-sensor is arranged in the flowing medium and the other UV-sensor in the reference space. Both UV-sensors are connected to a measuring and evaluating circuit, which compares and evaluates the signals of the UV-sensors.

11 Claims, 2 Drawing Sheets

DEVICE FOR THE CONTINUOUS DETERMINATION OF THE UV-TRANSMISSION THROUGH FLOWING OR RUNNING MEDIA

BACKGROUND OF THE INVENTION

1. Field of the Invention

The invention relates to a device for the continuous determination of a UV-transmission into flowing or running media, such as drinking water or purified waste water.

2. The Prior Art

The prior art has shown ways to disinfect microbiologically contaminated media by UV-irradiation. The disinfecting effect depends upon the condition or state of the medium. Contaminants in the form of dissolved or undissolved ingredients reduce the effective penetration depth in the UV-radiation. Therefore, it may be necessary to test media parallel with the UV-irradiation for their UV-transmission and thus for their suitability for disinfection by UV-irradiation.

Therefore, the invention is an improvement over the prior art because it provides a device for the determination of the effective UV-transmission depth into flowing media that provides a reliable evaluation.

SUMMARY OF THE INVENTION

This device overcomes measurement errors that could be caused by aging, temperature and flow variations, and other influences that could impair the radiation power of the UV-radiation source. These problems are avoided by employing the same UV-radiation source both for measuring the irradiation intensity in a flowing medium and in a reference space. The reference space is designed as a hollow space or cavity and may be filled with a medium that may be a solid, a liquid or a gas that is permeable to UV-radiation. It is possible also to use the same basic medium that is contained in the medium to be disinfected. Thus the reference medium can be filled with pure water so that it compares to waste water in the medium to be disinfected. It is also important to know the degree of UV-irradiation intensity damping in the medium in the reference space. Errors in measurement can be compensated by comparing the Pleasuring signals of the two UV-sensors.

The UV-sensors may be spaced apart from the emitting surface of the UV-radiation source at an equal distance or at a different distance. When spaced at an equal distance, the signals can be more simply processed so that the measuring signals of the two UV-sensors can be equally weighed. With different spacings, the measuring signals are weighed with reversed dependence on the spacing from the UV radiation emitting surface. This measurement takes into account that the intensity of irradiation decreases as the spacing from the emitting surface of the UV-radiation source increases.

The UV-sensors detect the radiation of the UV-radiation source preferably the center. Since the homogeneity of the radiation is particularly high in the center, particularly accurate measured values arc obtained.

If the reference space is not sealed against the measured medium, the sensors are spaced so that one UV-sensor is always arranged in the reference space and the other UV-sensor always in the flowing medium. These sensors are placed within the variation tolerance between the medium and the reference space. With this design, the sensors are positioned with the beast amount of spacing. Furthermore, this assures that the sensors detect about the same irradiation intensity range of the UV-radiation source and thus achieve high measuring accuracy.

Since the emitting surface of the UV-radiation has a specified minimum length of 13 cm, this source assures that there is a range or zone where the radiation intensity is homogeneous. This range is present in the center of the UV-radiation source. In addition a tail 5 cm in length extends the UV-radiation source, into the flowing medium and into the reference space. This design assures that ranges are available for each measurement where there is a constant radiation intensity.

The UV-radiation source is designed in the form of a cylindrical gas discharge lamp that is arranged in a protective tube. This tube projects partially into the flowing medium and partially into the reference space. The UV-radiation source can be employed in a drain normally used for disinfection to carry out the measurement there in any desired location. The cylindrical shape of the gas discharge lamp assures that an emitting surface can abut or adjoin both the medium and the reference space. Therefore, the same irradiation intensity of the UV-radiation source is available in both zones.

A cleaning device is associated with the UV-radiation source and the UV-sensor arranged in the flowing medium. Such a cleaning device prevents the formation of coatings on the UV-sensor and on the UV-radiation source. These coatings come from ingredients in the water, in the form of suspended substances. These coatings would grow over time and thereby increase the damping between the UV-radiation source and the UV-sensor, and falsify the measuring result. Cleaning the sensor assures that the measuring result exclusively relates to the UV-transmission of the medium itself.

In a preferred embodiment, the cleaning device comprises a first stripper for the UV-radiation source or its protective tube, and a second stripper for the UV-sensor. The two strippers are actuated at intervals by a common linear drive. By designing the cleaning device in the form of a stripper the flow of the radiation between the UV-radiation source and the UV-sensor is interrupted only for a short time. Therefore, the measurement, has to be interrupted only briefly as well. Due to such intermittent actuation, sufficiently long measuring periods are available, and the source is cleaned regularly. Therefore, the measurement can be viewed as being unimpaired by contaminations.

According to one embodiment, the first stripper forms a ring that encloses the UV-radiation source or its protective tube. In addition this ring can enclose this source or its tube partly in the form of ring segments. Furthermore, the second stripper is mounted on the ring or ring segment. The first and the second strippers are directly coupled to each other and are additionally guided on the UV-radiation source or its protective tube. Furthermore, this design assures that the first stripper from the UV-radiation source or its protective tube and the spacing of the second stripper from the UV-sensor are always optimally spaced.

BRIEF DESCRIPTION OF THE DRAWINGS

Other objects and features of the present invention will become apparent from the following detailed description considered in connection with the accompanying drawings which discloses two embodiments of the present invention. It should be understood, however, that the drawings are designed for the purpose of illustration only and not as a definition of the limits of the invention, In the drawings, wherein similar reference characters denote similar elements throughout the several views.

DETAILED DESCRIPTION OF PREFERRED EMBODIMENTS

Figure 1:
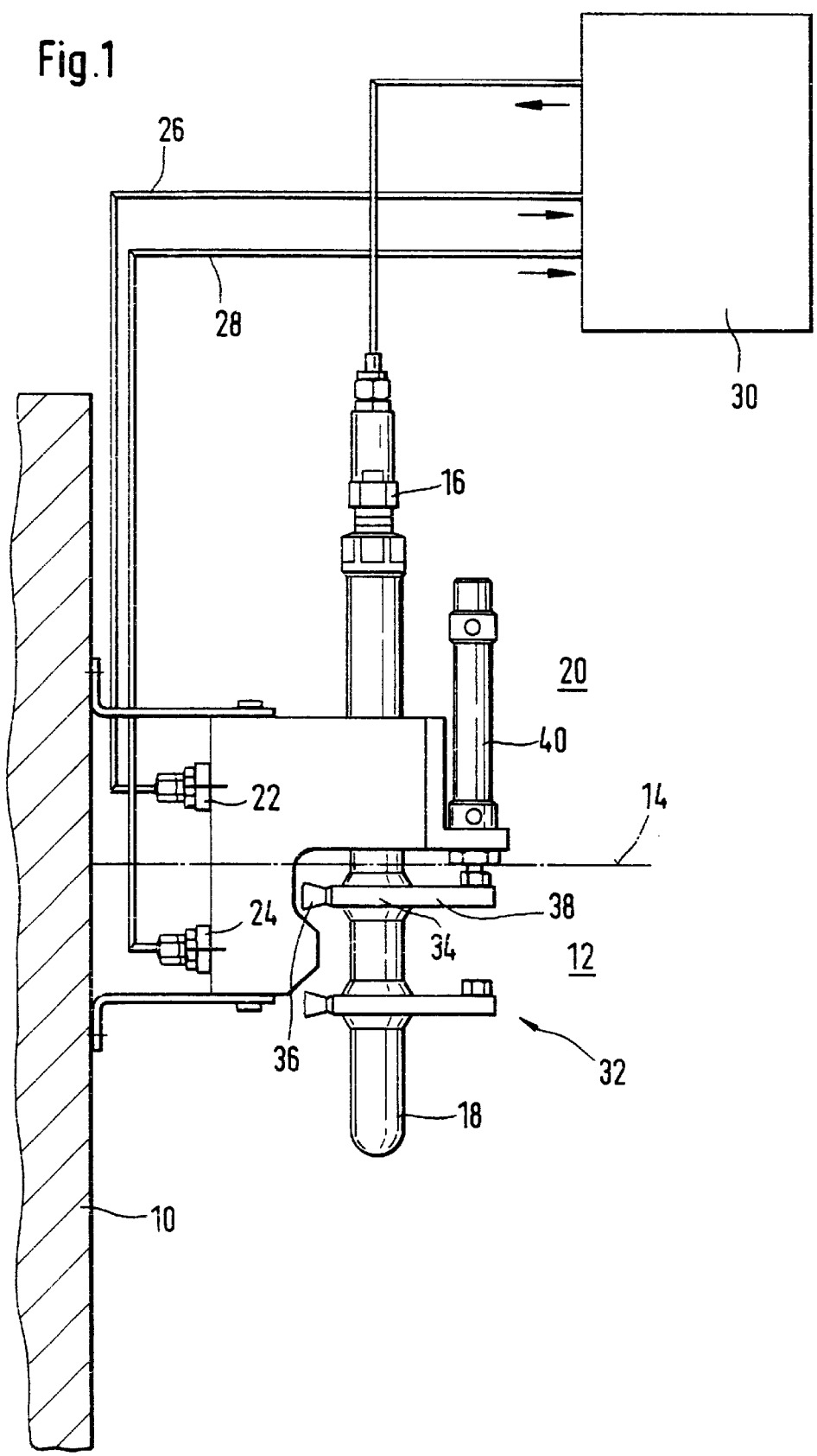
FIG. 1 shows a cross section through a drain with a first embodiment of a device.

FIG. 1 shows a first embodiment of the device disposed in a drain attached to a sectional piece of a wall 10 showing a flowing medium 12 that reaches level 14. A UV-radiation source 16 in a protective tube 18 is arranged in this drain. The protective tube 18 immerses partially in flowing medium 12, while another upper part is located outside of the flowing medium 12. This upper part forms a reference space 20 in an open type of construction. Reference space 20 is filled by ambient atmosphere. UV-sensors 22, 24 are arranged with equal spacings from protective tube 18 or UV-radiation source 16. One UV-sensor 22 is located above level 14 of medium 12 and thus in reference space 20, whereas the other UV-sensor 24 is arranged within flowing medium 12 and thus located below its level 14. Both UV-sensors 22 and 24 are disposed parallel to each other and are located in the same vertical plane.

Measuring lines or cables 26, 28 lead from the two UV-sensors 22, 24 to an evaluation circuit 30. This evaluation circuit 30 supplies energy at the same time for feeding UV-radiation source 16.

In addition, a cleaning device 32, is connected to protective tube 18. Cleaning device 32 comprises a first stripper 34 for UV-radiation source 16 or its protective tube 18, and a second stripper 36 for UV-sensor 24 located in medium 12. The first stripper 34 is designed in the form of a ring segment and partially encloses the protective tube 18 of UV-radiation source 16. The second stripper 36 is mounted on ring segment 38. The two strippers 34 and 36 are coupled to a lifting cylinder 40, with the lifting cylinder forming a linear drive. Lifting cylinder 40 is actuated intermittently, so that after a first stroke, strippers 34 and 36 are driven into an upper end position, and after a second stroke strippers 34 and 36 are driven into a lower end position. UV-radiation source 16 or its protective tube 18 are cleaned by the first stripper 34.

The measuring and evaluating circuit evaluates the measured values received from UV-sensors 22, 24 by comparing the radiation intensities picked up by the two UV-sensors 22, 24 with each other. Errors in measurement values can be corrected by comparing each measurement value with a reference value collected in reference space 20. These errors have been caused by temperature variations or ageing phenomena of UV-radiation source 6. The measured values related to a reference can then supply a statement on the UV-transmission of the flowing medium by linking the measured values tabularly or via an allocation function with defined UV-transmission criteria.

As a result of such evaluation, it is possible, to change the flow of medium 12 in the drain or the radiation power of UV-radiation source 16 to adapt the disinfecting effect to a changing UV-transmission. Also, a message can be issued if limit values are exceeded or not reached. For example, a message can be issued that states that the glowing medium 12 is excessively contaminated to a degree not permitting successful disinfection by UV-radiation.

Figure 2:
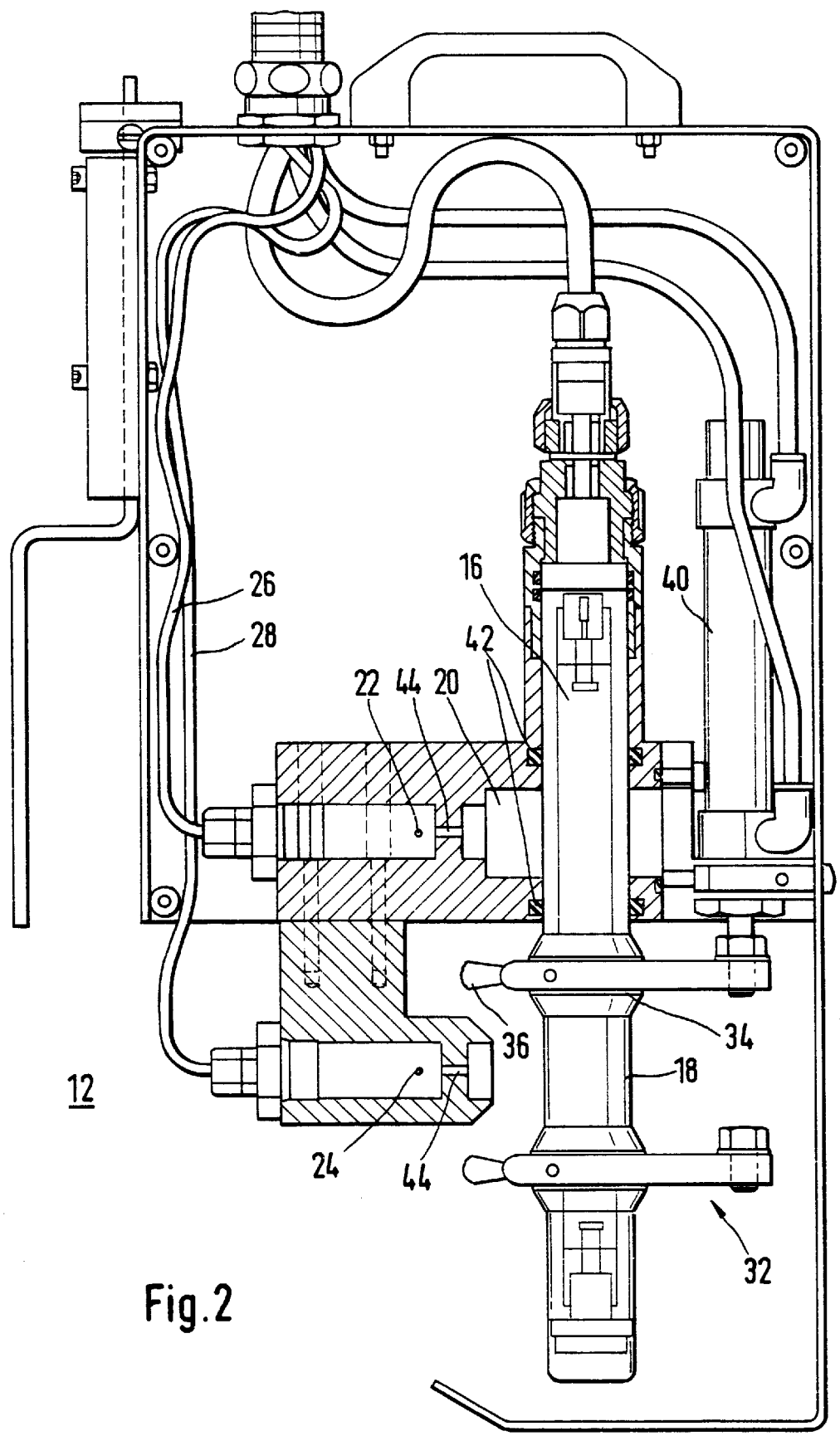
FIG. 2 is a a second embodiment of the device as shown in FIG. 1.

While the first embodiment in FIG. 1 shows that reference space 20 is open, the second embodiment according to FIG. 2 shows a closed reference space 20. This reference space is sealed against the flowing medium 12 by seals 42. Reference space 20 can be filled with a gaseous medium such as air or a protective gas. It is also possible to have a liquid or solid medium to prevent the formation of condensate in reference space 20 and to which may impair the transmission of the UV-radiation.

Furthermore, UV-sensors 22, 24 can be spaced at different distances from UV-radiation source 16. For example, UV-sensor 22 could be mounted in reference space 20 directly on the wall of protective tube 18. However, due to different spacings from UV-radiation source 16 it would be necessary to differently weigh the measuring signals.

So as to assure high accuracy and reproducibility of the measurement, shutters 44 are associated with UV-sensors 22, 24, which limit the aperture angle in a defined way.

Accordingly, while only a two embodiments of the present invention have been shown and described, it is to be understood that many changes and modifications may be made thereunto without departing from the spirit and scope of the invention as defined in the appended claims.

What is claimed is:

1. A device for the continuous determination of the UV-transmission of a flowing or running medium, which comprises:

a UV-radiation source irradiating a zone of the medium, respective zones of equal irradiation intensity of an emitting surface of the UV-radiation source extending into, or bordering, the medium and a reference space;

two UV-sensors directed at the respective zones of equal irradiation intensity, one of the UV-sensors being arranged in the medium and the other UV-sensor being arranged in the reference space;

a measuring and evaluating circuit connected to the two UV-sensors for comparing and evaluating signals emitted by the UV-sensors; and a cleaning device associated with the UV-radiation source and the UV-sensor arranged in the medium, the cleaning device comprising a first stripper for the UV-radiation source or a protective tube therefor and a second stripper for the UV-sensor, the first and second strippers being actuated intermittently by a common linear drive.

2. The device according to claim 1, wherein the reference space is a hollow space, which is empty or filled with a medium permeable to UV-radiation.

3. The device according to claim 2, wherein the medium permeable to UV-radiation is a solid, a liquid or a gaseous medium.

4. The device according to claim 3, wherein the medium permeable to UV-radiation is the same medium as the flowing or running medium.

5. The device according to claim 1, wherein said two UV-sensors are spaced apart at an equal distance from the emitting surface of the UV-radiation source, and wherein a series of output signals from said two sensors are weighed equally.

6. The device according to claim 1, wherein said two UV-sensors are spaced apart at different distances from the emitting surface of said UV-radiation source, and a series of output signals from said two sensors are weighed with reversed dependence on the spacing distances from the emitting surface of the UV-radiation source.

7. The device according to claim 1, wherein the UV-sensors detect the radiation of the UV-radiation source in a center region of said source.

8. The device according to claim 1, further comprising at least one seal for sealing said reference space from the medium, wherein said two UV-sensors are spaced apart at such a distance that, within the variation of tolerance of the phase limits between the medium and the reference space, one of the UV-sensors is arranged in the reference space and the other UV-sensor is arranged in the medium.

9. The device according to claim 1, wherein the emitting surface of the UV-radiation source is at least 13 cm long and extends at least 5 cm into the medium and at least 5 cm into the reference space.

10. The device according to claim 1, wherein the UV-radiation source is a cylindrical gas discharge lamp arranged in a protective tube, said tube partly projecting into the medium and partly into the reference space.

11. The device according to claim 1, wherein the first stripper encloses the one UV-radiation source or its protective tube in the form of a ring, and said second stripper is mounted on said ring.

* * * * *